United States Patent
Yang et al.

(10) Patent No.: US 7,387,439 B2
(45) Date of Patent: Jun. 17, 2008

(54) X-RAY BEAM CALIBRATION FOR BONE MINERAL DENSITY ASSESSMENT USING MAMMOGRAPHY SYSTEM

(75) Inventors: Chang-Ying J. Yang, Webster, NY (US); Zhimin Huo, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 11/355,040

(22) Filed: Feb. 15, 2006

(65) Prior Publication Data
US 2007/0189453 A1     Aug. 16, 2007

(51) Int. Cl.
G01D 18/00      (2006.01)
G01N 23/06      (2006.01)
G01N 23/04      (2006.01)

(52) U.S. Cl. .................. 378/207; 378/51; 378/54; 378/56

(58) Field of Classification Search .............. 378/4, 378/18, 50–56, 162, 204, 207, 8
See application file for complete search history.

(56) References Cited

U.S. PATENT DOCUMENTS

| | | | |
|---|---|---|---|
| 4,811,373 A | | 3/1989 | Stein |
| 5,335,260 A | * | 8/1994 | Arnold ..................... 378/207 |
| 5,493,601 A | * | 2/1996 | Fivez et al. ............... 378/207 |
| 5,673,303 A | * | 9/1997 | Hangartner ............... 378/207 |
| 5,712,892 A | | 1/1998 | Weil et al. |
| 6,246,745 B1 | | 6/2001 | Bi et al. |
| 6,816,564 B2 | | 11/2004 | Charles, Jr. et al. |
| 6,824,309 B2 | * | 11/2004 | Robert-Coutant et al. .. 378/207 |
| 2001/0004394 A1 | * | 6/2001 | Siffert et al. .............. 378/56 |
| 2002/0114425 A1 | | 8/2002 | Lang et al. |
| 2002/0150205 A1 | * | 10/2002 | Adriaansz ................. 378/54 |
| 2004/0028181 A1 | | 2/2004 | Charles, Jr. et al. |
| 2004/0077088 A1 | * | 4/2004 | Charles, Jr. et al. ....... 435/455 |
| 2005/0031181 A1 | | 2/2005 | Bi et al. |
| 2005/0059875 A1 | | 3/2005 | Chung et al. |
| 2006/0072706 A1 | * | 4/2006 | Russell ..................... 378/162 |

OTHER PUBLICATIONS

Huo, U.S. Appl. No. 60/755,233, Bone Mineral Density Assessment Using Mammography, filed Dec. 30, 2005.

* cited by examiner

*Primary Examiner*—Irakli Kiknadze

(57) ABSTRACT

An apparatus and method calibration method, particularly to determine an x-ray generation technique to acquire a hand x-ray image using a mammography x-ray system for assessing Radiographic Absorptiometry (RA) based BMD (Bone Mineral Density).

14 Claims, 4 Drawing Sheets

X-RAY BEAM CALIBRATION FOR BONE MINERAL DENSITY ASSESSMENT USING MAMMOGRAPHY SYSTEM

FIELD OF THE INVENTION

The invention relates generally to the field of mammography imaging. More specifically, the invention relates to x-ray beam calibration when assessing Radiographic Absorptiometry (RA) based BMD (Bone Mineral Density) using a mammography imaging system.

BACKGROUND OF THE INVENTION

Osteoporosis is a skeletal disorder characterized by reduced bone strength. It can result in increased risk to fractures, height loss, hunched backs, and pain. Bone strength is a function of bone mineral density (BMD) and bone quality. It is believed that bone mineral density peaks about the age of 30 for both men and women, and then declines gradually. Some statistics have indicated that Osteoporosis affects approximately 20 million people and is a cause of about 1.3 million fracture incidents in the United States each year. As such, screening for bone mineral density is often desired.

Several common techniques have been used to measure bone mineral density, including but not limited to bone puncture, radiation Absorptiometry of single energy x-ray systems, DEXA (dual energy x-ray Absorptiometry), and sonography.

Bone puncture can be an accurate but invasive procedure, which involves the extraction of bone mass from spine area. Such a procedure carries risk.

With regard to single energy x-ray systems, mineral loss in a person's bones can be estimated from a single energy x-ray image of a body part. In diagnosing and treating bone diseases, it is common to take radiographic images of the patient (e.g., skeletal features of the patient), then either read the images directly or perform software analysis on the images to extract information of interest. For example, in diagnosing or monitoring the treatment of Osteoporosis, one might take x-ray images of selected skeletal bones, then perform computer analysis on certain image features to determine bone volume, bone length, bone geometric changes, bone strength conditions, bone age, bone cortical thickness, and bone mineral mass.

Typically, when reading and interpreting radiographic images directly, the treating physician will refer the patient to a radiologist, who can supervise both taking the radiographic image and interpreting the image to extract desired bone information, such as bone mass and bone contour irregularities. Alternatively, if the bone analysis is done, at least partially, by a computer analysis system, the x-ray images prepared by the radiologist may be sent back to the treating physician's computer site or to another computer site for computer analysis.

DEXA is a device used by hospitals to measure bone mineral density (BMD). In DEXA, two low-dosage x-ray beams with differing energy levels are directed at a patient's spine, hip, or whole body using conventional x-ray machines. A computer calculates the content of bone mineral density based on the relationship that different bones absorb different energy levels. While some consider DEXA to be accurate, the apparatus is bulky and expensive. U.S. Pat. No. 6,816,564 (Charles, Jr.) is directed to a technique for deriving tissue structure from multiple projection dual-energy x-ray Absorptiometry.

Sonography devices measure the bone mineral density of peripheral bones, such as a heel, shin bone, or kneecap. It is recognized that the bone mineral density in the spine or hip change faster than that in heel, shin bone, or kneecap. Thus, sonography is considered by some to be not as accurate or sensitive as DEXA in the determination of bone mineral density. DEXA allows early detection of abnormal change in bone mass for its targets spine, hip, or whole body. However, sonography offers advantages of lower cost and radiation-free.

U.S. Pat. No. 6,246,745 (Bi) describes a software system for determining bone mineral density from radiographic images of a patient hand obtained from conventional x-ray imaging system.

U.S. Patent Application No. 2005/0059875 (Chung) describes a biosensor and method for bone mineral density measurement.

U.S. Patent Application No. 2005/0031181 (Bi) is directed to a system and method for analyzing bone conditions using DICOM compliant bone radiographic images.

U.S. Pat. No. 5,712,892 (Weil), commonly assigned, is directed to an apparatus for measuring the bone mineral content of an extremity.

While such systems may have achieved certain degrees of success in their particular applications, there is a need for a system and method for bone mineral density screening, particularly wherein a medical professional can readily and locally (e.g., at an office location) generate a bone mineral density report. A suitable system would be easy to use, reduced in cost, yet provide sufficient accuracy. Preferred would be an on-site screening that can be utilized by physicians, radiologists, or other medical professionals.

U.S. Provisional Patent Application No. 60/755,233 (Huo), titled BONE MINERAL DENSITY ASSESSMENT USING MAMMOGRAPHY SYSTEM, filed on Dec. 30, 2005, commonly assigned, and incorporated herein by reference, describes an imaging system and method to acquire hand x-ray images suitable for bone mineral density (BMD) screening and analysis using a mammography x-ray imaging system.

Because of the challenges to acquire hand images with adequate quality using a mammography system, there exists a need to establish a calibration procedure to perform quality assurance of the x-ray system before acquiring patient images.

SUMMARY OF THE INVENTION

The present invention provides an x-ray beam calibration apparatus and a method for BMD screening and analysis when using a mammography imaging system to acquire extremity x-ray images, such as a hand. The apparatus and the method described can be employed prior to the acquisition of any patient image on a mammography imaging system to determine the proper x-ray techniques for an average patient. The selection of proper x-ray techniques promotes adequate image capture quality suitable for subsequent image analysis.

Any objects provided are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided an apparatus/object/member comprised of x-ray attenuation material of different thicknesses in several steps.

Each step of a given thickness provides sufficient uniform area of equal thickness to allow accurate measurement of optical density (OD) in an x-ray film or accurate measurement of pixel values in a digital x-ray image of the that step in the object.

According to an aspect of the invention, a set of rules/procedures regarding the OD values in the x-ray film or pixel values in the digital image of the calibration member corresponding to the steps of different thickness of x-ray attenuation material are established/used to reject or accept the image quality.

According to another aspect of the present invention, there is provided an x-ray beam calibration method with procedures to use the x-ray images of the calibration member to determine a proper x-ray technique for acquiring images of an average patient in order to achieve adequate image quality for BMD assessment.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
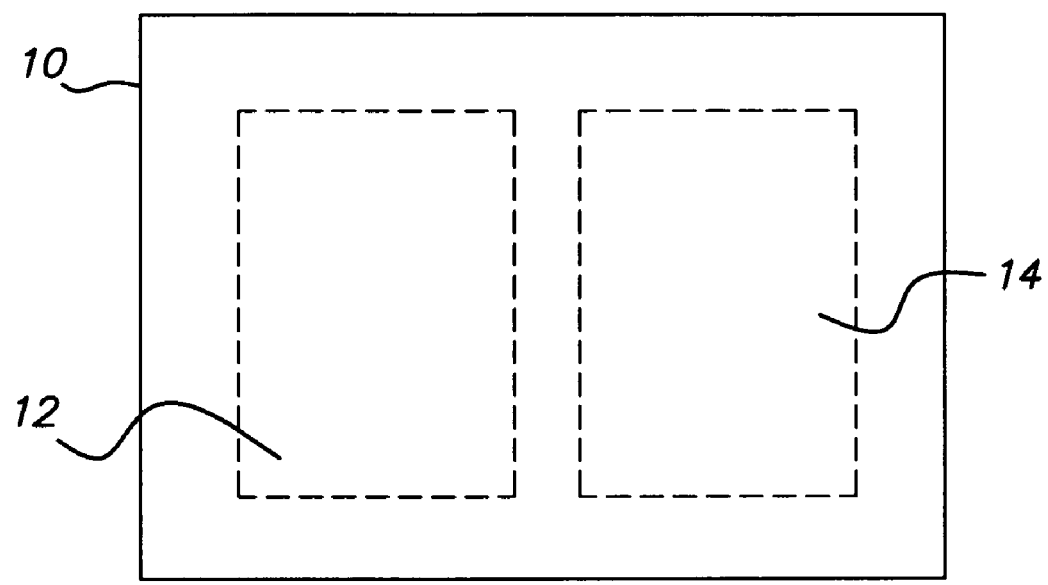
FIG. 1 shows an illustration of an calibration member in accordance with the present invention.

The following is a detailed description of the preferred embodiments of the invention, reference being made to the drawings in which the same reference numerals identify the same elements of structure in each of the several figures.

It is noted that the American Cancer Society recommends that women over the age of 40 years obtain annual mammograms. Millions of women have their annual screening mammograms each year at hospitals or breast imaging centers. Accordingly, Applicants have noted it would be desirable for women to have both their annual mammography screening and a bone mineral density screening done in one visit, at one location, and using one imaging system.

Conventionally, extremities (e.g., hands and feet) are imaged using conventional x-ray system, which generates an x-ray beam adapted to capture both low and high-density objects (i.e., bone and soft tissue) on a detector (film or digital) that are designed with a wide dynamic range. In contrast, mammography imaging systems are configured for high contrast (i.e., narrow dynamic range) to image the soft tissue in the breast for the purpose of detection and diagnosis of breast cancer.

U.S. Provisional Patent Application No. 60/755,233 (Huo), titled BONE MINERAL DENSITY ASSESSMENT USING MAMMOGRAPHY SYSTEM, filed on Dec. 30, 2005, commonly assigned, and incorporated herein by reference, describes an imaging system and method to acquire hand x-ray images suitable for bone mineral density (BMD) screening and analysis using a mammography x-ray imaging system. A treating physician or a computer aided system or computer aided diagnosis (CAD) system can then analyze the acquired images for bone mineral density (BMD) loss assessment. It is intended that the use of a mammography imaging system to acquire extremity images such as hand for assessing BMD can improve the workflow and access for women to BMD exams, so as to reduce the cost and improve the efficiency of screening.

One method of performing the BMD analysis on the patient images is done by computer assisted diagnosis (CAD) software running on a computer system. However, in order to have an accurate and reliable assessment of the BMD analysis by the CAD software, the patient images provided for the analysis must have suitable/adequate quality regarding the image information available for assessment. In the example of imaging hand for CAD BMD analysis, both the soft tissue and the details of the phalanges or metacarpal bones need to be properly presented in the image. This may not always be the case for the patient images acquired on a mammography imaging system.

For mammography imaging system using a conventional analog screen/film system to capture patient images, the film needs to be processed first after x-ray exposure. The processed film is then digitized by a film digitizer if an analysis by a computer CAD software is desired. In this process, the type of the screen/film system, the x-ray techniques selected for exposure, the type and the conditions of the film processor and the film digitizer can all impact the quality of the final digital images presented to the computer CAD software.

In many situations, the screen/film system and the type of the film processor are selected or optimized for the purpose of imaging breast tissue (e.g., mostly soft tissues) and not for imaging a hand. The variations in the condition of the chemicals in the processor can affect the image quality significantly. It is therefore not economically feasible to maintain a constant processor condition in most places. Additionally, the film digitizer can also impose limitations on the image quality if not selected properly. What remains to control for the technologists when acquiring images to ensure the quality of the digitized patient images for RA BMD assessment is the selection of the x-ray techniques.

Similar situations can exist for mammography imaging systems using digital x-ray detectors even though fewer components are involved in the imaging chain. These digital detectors are optimized for imaging breast tissue and the largest amount of x-ray radiation the detector can detect without saturation is often limited. The noise performance of the detector at low signal level can also potentially limit the proper detection of the details of the phalanges or metacarpal bones. Again, the technologists need to carefully select the x-ray techniques when acquiring patient images to ensure the quality suitable for computer software BMD assessment.

X-ray techniques/parameters selectable by a technologist when acquiring images include kVp or tube voltage (which controls the maximum energy of the x-ray) and mAs or milliamps-second (which controls the intensity of the x-ray). On some mammography x-ray machines, a choice of a target used for x-ray generation and a filtration are also available.

The x-ray spectrum generated with the exact same values of x-ray techniques from different mammography x-ray machines are generally different due to differences in the aging of the machine, different designs from different manufactures, and the like. The technologists must configure the machine to find the proper x-ray techniques suitable for the average size patients on the particular mammography imaging system intended to be used for RA BMD assessment. Based on the x-ray techniques suitable for average size patient, the technologists need to make further detail adjustment on the choice of x-ray techniques taking into consideration of the actual hand size of each individual patient.

The present invention describes an apparatus and a method to determine the proper x-ray techniques suitable for average patient on a particular mammography imaging system, prior to the acquisition of any patient image.

The present invention describes the imaging of a hand for RA BMD analysis on a mammography imaging system as an example. It is noted that other extremities can be imaged. That is, it is envisioned to extend the method of the present invention with suitable modification on the design of the calibration member for imaging other extremities (e.g., an elbow) for RA BMD analysis on a mammography imaging system.

Figure 2:
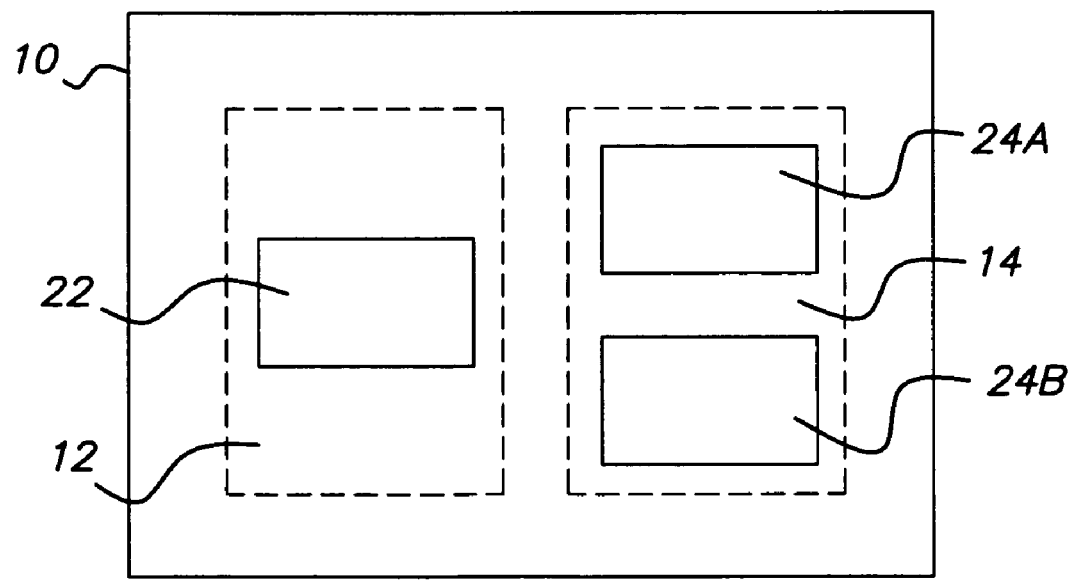
FIG. 2 shows another illustration of the calibration member of FIG. 1.

FIGS. 1 and 2 show an exemplary calibration member 10 in accordance with the present invention. Calibration member 10 includes at least two portions: a first portion 12 and a second portion 14. First portion 12 comprises x-ray attenuation material simulating thickness of soft tissue in the extremity. Second portion 14 comprises x-ray attenuation material simulating thickness of bones in the extremity.

As best shown in FIG. 2, first portion 12 comprises x-ray attenuation material simulating at least one thickness of soft tissue in the extremity, and second portion 14 comprises x-ray attenuation material simulating at least two different thicknesses of bones in the extremity. An object/phantom 22 (disposed in first portion 12) comprises attenuating material simulating at least one thickness of soft tissue in the extremity. At least two objects/phantoms 24A, 24B (disposed in second portion 14) comprises x-ray attenuation material, each simulating a different thickness of bones in the extremity.

Figure 3:
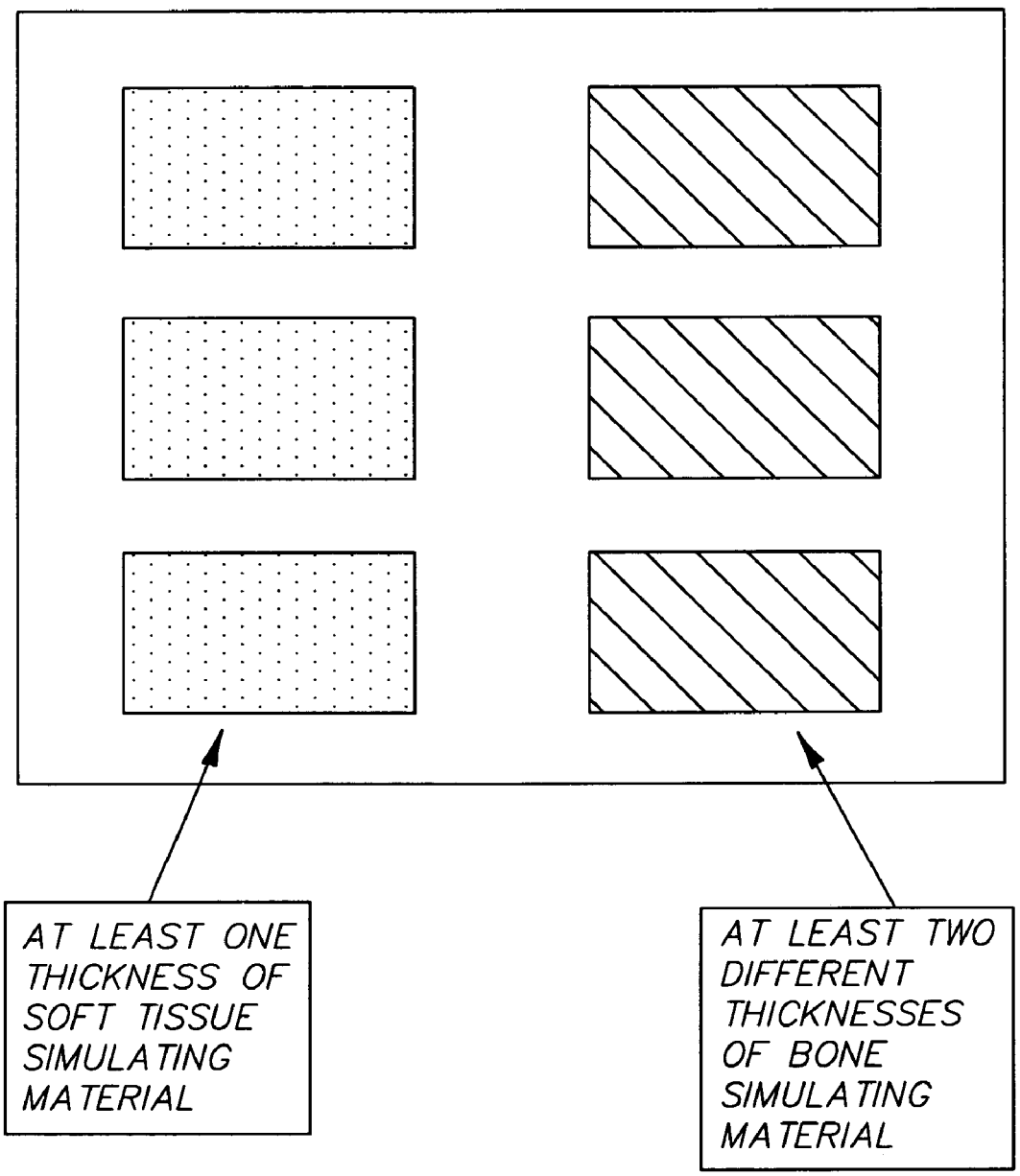
FIG. 3 shows a further illustration of the calibration member of FIGS. 1 and 2.

It is noted that other numbers of phantoms can be employed. For example, FIG. 3 shows a further configuration of calibration member 20 having three phantoms 22 disposed in first portion 12 and three phantoms disposed in second portion 14.

Further, while the figures show the phantom as having a rectangular shape, such a showing is for exemplary purposes only, and other shapes can be employed.

Each phantom is comprised of either the same or different x-ray attenuation material of different distinct thicknesses. For each of the distinct thickness, the phantom includes an area of uniform thickness made of the same x-ray attenuation material. The size of the area of the uniform thickness for each distinct thickness in the phantom is sufficiently large to provide reliable measurement of the OD (optical density) in the x-ray film or measurement of the pixel value in the digital image of that uniform thickness area in the phantom.

The measured OD in the x-ray film or measurement of the pixel values in the digital x-ray images of the calibration member can be referred to as a calibration measurement.

With regard to first portion 12, at least one (but not limited to one) calibration phantom of a distinct thicknesses of a x-ray attenuation material simulates the x-ray attenuation properties of the soft tissue in an average size hand under a typical mammography x-ray spectrum. An example of the material that can be employed is aluminum of thickness ranging from about 0.5 to about 1 mm. Another example of the material that can be employed is polymethyl methacrylate (PMMA or acrylic) of thickness ranging from about 5 to about 15 mm. Other soft tissue equivalent material such as epoxy resin of thickness ranging from 5 to 15 mm can also be employed.

With regard to second portion 14, at least two (but not limited to two) calibration phantoms of different thicknesses of an x-ray attenuation material should simulate the x-ray attenuation properties of the bones in an average size hand under a typical mammography x-ray spectrum. An example of the material that can be employed is aluminum of thickness ranging from about 1 to about 10 mm with the difference between any of the two consecutive phantom thicknesses ranging from about 0.1 to about 1 mm. Bone equivalent material of thickness ranging from about 2 to about 15 mm with the difference between any of the two consecutive phantom thicknesses in calibration member 10 ranging from about 0.1 to about 1 mm.

Threshold values is employed. More particularly, in the present invention, threshold values are determined for the measured OD in the x-ray film or pixel values in the digital x-ray images of the calibration member. This set of threshold values is employed to determine if the x-ray techniques used to generate the x-ray film or digital image is adequate/suitable. If the x-ray film or digital image failed to meet any one of the requirements (as will be described below), the x-ray techniques used to acquire the image of the extremity is considered inadequate.

More particularly, calibration member 10 is imaged using a particular x-ray technique setup by the technician. If the x-ray film or digital image captured using the particular setup fails to meet any one of the requirements (as will be described below), the particular x-ray technique used to acquire the image is considered inadequate to capture both soft and bone tissue.

For the x-ray attenuation material (phantom 22) simulating the soft tissue in an average size hand (whether there is one or more than one phantom), the measured OD in the x-ray film of the phantom area should not be greater than a threshold value: $OD_S$. The value of $OD_S$ is selected as being equal to a certain/predetermined value (for example, 0.2) below the maximum OD of the imaging chain. The maximum OD of the imaging chain, in the case that a film digitizer was employed to digitize the x-ray film for CAD BMD assessment, is the lower value of the two possible candidates. The first candidate is the maximum attainable OD on the film due to the combination of the screen/film system and the film processor used. The second candidate is the maximum OD that the film digitizer is capable of faithfully digitizing without biasing the average digitized value by the noise of the signal or other limitations such as signal saturation of the digitizer. The maximum OD of the imaging chain is the lower value of the two candidates.

When a digital detector has been employed to acquire the digital image of calibration member 10 (and accordingly, imaging the phantom simulating the soft tissue in an average size hand), the measured average pixel value of the phantom area should not be greater than a threshold value: $PV_S$. The value of $PV_S$ is determined by the digital detector used, which should correspond to the signal at certain/predetermined percentage level, such as 85% to 90%, of the maximum detector signal level without the average pixel value in the digital image biased by signal saturation or other limitations of the detector.

With regard to the phantoms for simulating the bones in an average size hand (whether there are two or more than two distinct thicknesses of the material in the object), the measured differences in OD in the x-ray film of the phantom areas between any two consecutive distinct thicknesses should be greater than a threshold value: $\Delta OD_B$, which should be at least the precision of the device that is used for measuring OD, such as 0.001 on a typical densitometer commonly used in a mammography imaging facility.

When a digital detector has been employed to capture the digital image of phantoms 24A,24B of calibration member 10 simulating the bones in an average size hand (whether there are two or more than distinct thicknesses of the material in the object), the measured differences in average pixel value of that part of the phantoms between any two consecutive distinct thicknesses should be greater than a threshold value: $\Delta PV_B$, which should be at least 1 pixel value, depending on the sensitivity of the pixel value as a function of the amount of x-ray radiation.

Accordingly, a method is now described for employing calibration member 10 to determine if an particular x-ray technique (which has been setup by a technician) is suitable for imaging an extremity, which for descriptive purposes, is a hand.

The method includes using an x-ray image of the extremity captured using film or in digital format, determining threshold values, and measuring the OD of the phantom areas of the captured image so as to guide an operator/technician to find an adequate x-ray technique suitable for the patient with an average size hand. The method is now more particular described with reference to FIGS. 4 and 5.

Figure 4:
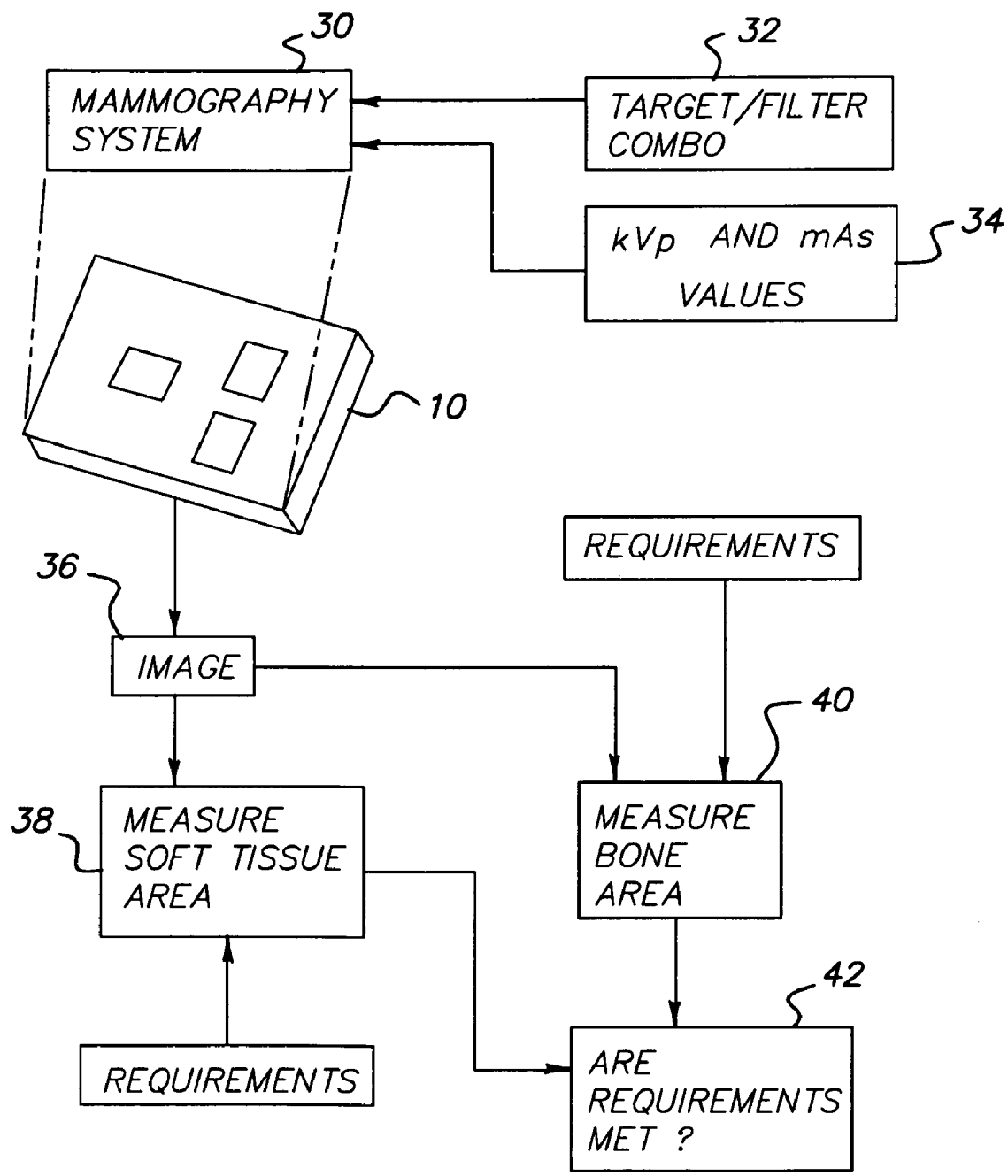
FIG. 4 is a diagrammatic view of a method in accordance with the present invention.
Figure 5:
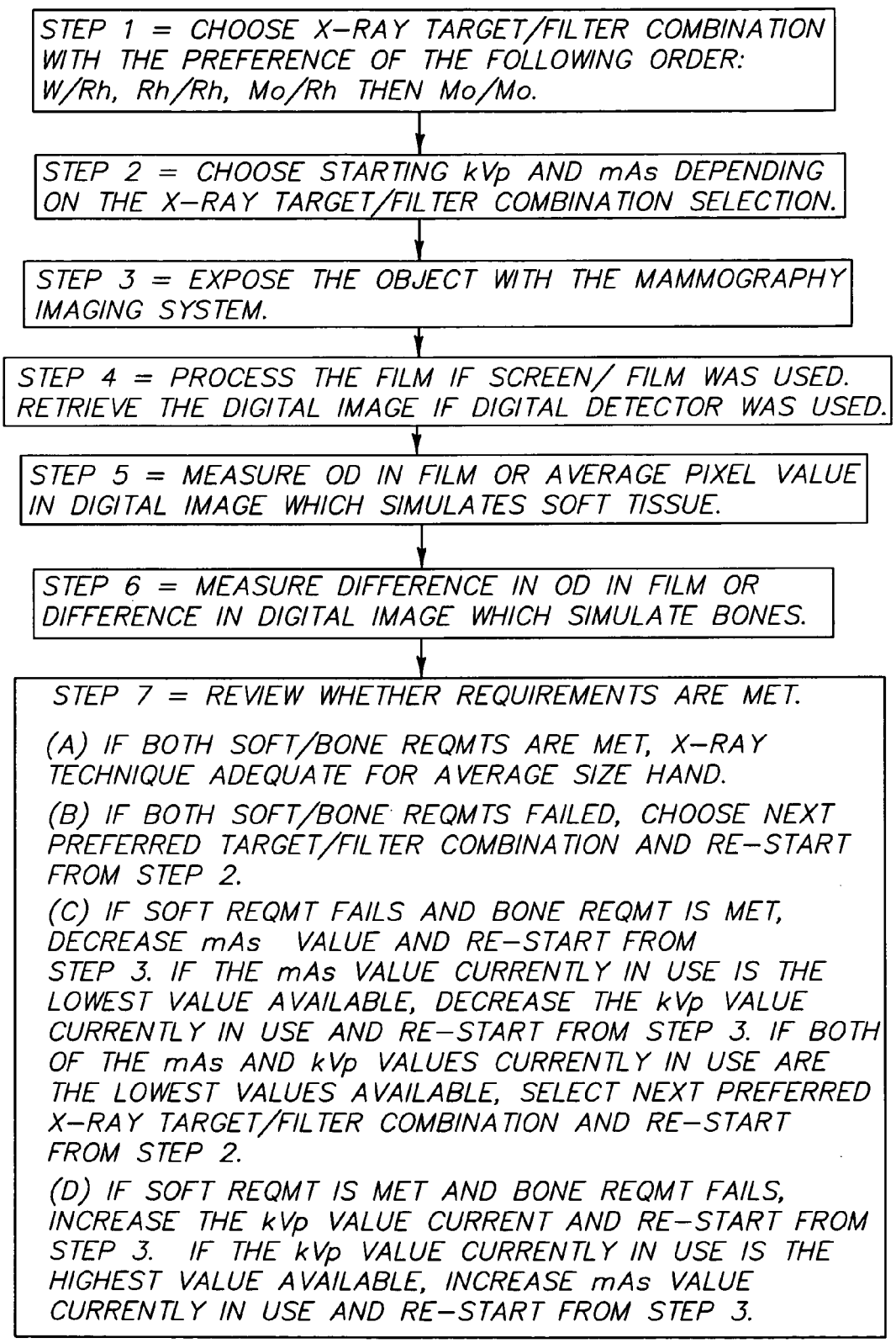
FIG. 5 shows a flowchart illustrating a method in accordance with the present invention.

A mammography system 30 is use to capture an image of calibration member 10. Since mammography systems employ different x-ray target/filter combinations, the technician makes a selection of a suitable x-ray target/filter combination which is available on the particular mammography machine being used. A preference of the target/filter combination is, in the following order: W/Rh, Rh/Rh, Mo/Rh, then Mo/Mo. (W refers to tungsten, Rh refer to Rhomdim, and Mo refers to molybdenum.) This selection is shown in FIG. 4 at box 32.

As shown at box 34, the technician selects initial kVp and mAs values. As is known to those skilled in the art, such a selection is dependent on the x-ray target/filter combination selection.

Calibration member 10 is then exposed using mammography system 30, and an image is obtained (box 36). It is noted, that if conventional film was used, the film needs to be processed. If a digital detector was used, the digital image is accessed.

The image of calibration member 10 is then reviewed.

More particularly, the image of phantom 22 (disposed in first portion 12) is reviewed with regard to the soft tissue. The optical density of the imaged area of phantom 22 is measured by measuring the optical density (OD) of the film or average pixel value in the digital image (that simulates soft tissue). Refer to box 38.

The measured values are then compared with the requirements. For the soft tissue, the measured value is compared with a predetermined value. For film, as described above, the measured OD in the x-ray film of the phantom area should not be greater than a threshold value: $OD_S$. For digital, as described above, the measured average pixel value of the phantom area should not be greater than a threshold value: $PV_S$.

The image of the phantoms of second portion 14 are reviewed with regard to the bone. That is, the image of phantoms 24A, 24B (disposed in second portion 14) are reviewed. The difference in OD in the film or the difference in the digital image between any two consecutive phantoms are measured. Refer to box 40.

The measured difference is then compared with the requirements. For the bone, the measured difference is compared with a predetermined value. For film, as described above, the measured differences in OD in the x-ray film of the phantom areas between any two consecutive distinct thicknesses should be greater than a threshold value: $\Delta OD_B$. For digital, as described above, the measured differences in average pixel value of that part of the phantoms between any two consecutive distinct thicknesses should be greater than a threshold value: $\Delta PV_B$.

The requirements are then reviewed to determined if both or one have been met (box 42).

If both requirements for soft tissue and bones are met, then the x-ray technique selected for imaging the calibration member should be adequate for imaging a patient having an average size hand.

If both requirements for soft tissue and bones failed, then it is suggested that the technician choose the next preferred x-ray target/filter combination available (box 32) on the mammography system, choose a new kVp and mAs, and re-image the calibration member.

If the requirement for soft tissue fails and the requirement for the bones is met, then it is suggested that the technician decrease the mAs value currently in use for the new x-ray technique and reimage the calibration member. If the mAs value currently in use is the lowest value available on the mammography system, decrease the kVp value currently in use for the new x-ray technique and reimage the calibration member. If both of the mAs and kVp values currently in use are the lowest values available, it is suggested to select the next preferred x-ray target/filter combination, choose new kVp and mAs values, and reimage.

If the requirement for soft tissue is met and the requirement for the bones fails, it is suggested to increase the kVp value currently in use for the new x-ray technique and reimage. If the kVp value currently in use is the highest value available on the mammography system, it is suggested to increase the mAs value currently in use for the new x-ray techniques and image.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A calibration method for a radiography system comprising the steps of:
   providing a calibration member having a first portion comprised of x-ray attenuation material simulating x-ray attenuation properties of soft tissue and a second portion comprised of x-ray attenuation material simulating x-ray attenuation properties of bone;

imaging the calibration member to generate a calibration image, the calibration image including a first and second imaged portion representing the first and second portions, respectively;

determining a soft calibration measurement of the first imaged portion;

determining a bone calibration measurement of the second imaged portion;

providing a soft tissue calibration threshold value;

providing a bone calibration threshold value;

comparing the soft tissue calibration threshold value with the soft calibration measurement;

comparing the bone calibration threshold value with the bone calibration measurement; and configuring the radiography system in response to the steps of comparing.

2. The method of claim 1, wherein the first portion comprises at least one calibration phantom of a distinct thickness of a x-ray attenuation material simulating the x-ray attenuation properties of soft tissue, and the second portion comprises at least two calibration phantoms of different thicknesses of an x-ray attenuation material simulating the x-ray attenuation properties of bone.

3. The method of claim 1, wherein the step of comparing the soft tissue calibration threshold value with the soft calibration measurement is accomplished by detennining whether the soft calibration measurement is less than the soft tissue calibration threshold.

4. The method of claim 1, wherein the step of comparing the bone calibration threshold value with the bone calibration measurement is accomplished by determining whether the bone calibration measurement is greater than the bone calibration threshold.

5. The method of claim 1, wherein the second portion comprises at least two calibration phantoms of different thicknesses of an x-ray attenuation material simulating the x-ray attenuation properties of bone, and the step of comparing the bone calibration threshold value with the bone calibration measurement is accomplished by:
   determining a bone calibration measurement for each of the two calibration phantoms;
   determining a difference between the two calibration measurements; and
   determining if the difference is greater than the bone calibration threshold.

6. The method of claim 1, wherein the soft calibration measurement is a measured optical density if the generated calibration image is an x-ray film image or a measurement of the pixel values if the generated calibration image is a digital x-ray image.

7. The method of claim 1, wherein the calibration method is acceptable if:
   the soft tissue calibration threshold value is greater than the soft calibration measurement; and
   the bone calibration measurement is greater than the bone calibration threshold value.

8. A computer storage medium having instructions stored therein for causing a computer to perform a calibration method comprising the steps of:
   providing a calibration member having a first portion comprised of x-ray attenuation material simulating x-ray attenuation properties of soft tissue and a second portion comprised of x-ray attenuation material simulating x-ray attenuation properties of bone;
   imaging the calibration member to generate a calibration image, the calibration image including a first and second imaged portion representing the first and second portions, respectively;
   determining a soft calibration measurement of the first imaged portion;
   determining a bone calibration measurement of the second imaged portion;
   providing a soft tissue calibration threshold value;
   providing a bone calibration threshold value;
   comparing the soft tissue calibration threshold value with the soft calibration measurement; and
   comparing the bone calibration threshold value with the bone calibration measurement.

9. A calibration method for a mammography x-ray system for assessing bone density, the method comprising the steps of:
   providing a calibration member having a first and second portion, the first portion comprising at least one soft calibration phantom of a distinct thickness of a x-ray attenuation material simulating the x-ray attenuation properties of soft tissue, and the second portion comprising at least two bone calibration phantoms of different thicknesses of an x-ray attenuation material simulating the x-ray attenuation properties of bone;
   imaging the calibration member to generate a calibration image, the calibration image including imaged portions of the soft calibration phantom and bone calibration phantoms;
   providing a soft tissue calibration threshold value;
   determining a soft calibration measurement of the soft calibration phantom imaged portion;
   comparing the soft tissue calibration threshold value with the soft calibration measurement;
   providing a bone calibration threshold value;
   determining a bone calibration measurement for each of the bone calibration phantom imaged portions;
   determining a difference between the two bone calibration measurements;
   determining if the difference is greater than the bone calibration threshold; and
   comparing the bone calibration threshold value with the difference; and
   configuring the mammography x-ray system in response to the steps of comparing.

10. The method of claim 9, wherein the soft calibration measurement is a measured optical density if the generated calibration image is an x-ray film image or a measurement of the pixel values if the generated calibration image is a digital x-ray image.

11. The method of claim 10, wherein the calibration method is acceptable if:
   the soft tissue calibration threshold value is greater than the soft calibration measurement; and
   the difference is greater than the bone calibration threshold value.

12. A calibration apparatus for use in a mammography x-ray calibration system prior to the acquisition of any patient image, comprising;
   a first portion comprising at least one calibration phantom of a distinct thickness of an x-ray attenuation material simulating the x-ray attenuation properties of soft tissue; and
   a second portion comprising a plurality of calibration phantoms of different thicknesses of an x-ray attenuation material simulating the x-ray attenuation properties of bone, wherein the plurality of bone calibration phantoms are comprised of aluminum and wherein a thickness difference between two consecutive phantoms is about 0.1 mm.

13. The apparatus of claim 12, wherein the soft tissue calibration phantom is comprised of aluminum having a thickness ranging from about 0.5 to about 1 mm.

14. The apparatus of claim 12, wherein the soft tissue calibration phantom is comprised of polymethyl methacrylate (PMMA or acrylic) having a thickness ranging from about 5 to about 15 mm.

* * * * *